United States Patent [19]
Martin

[11] Patent Number: 5,055,268
[45] Date of Patent: Oct. 8, 1991

[54] AIR-BORNE ALCOHOL SENSOR

[75] Inventor: Peter G. Martin, Mercer Island, Wash.

[73] Assignee: Easterm Electronics Manufacturing Corp., East Harford, Conn.

[21] Appl. No.: 565,871

[22] Filed: Aug. 8, 1990

Related U.S. Application Data

[63] Continuation of Ser. No. 463,930, Jan. 8, 1990, abandoned, which is a continuation of Ser. No. 244,580, Sep. 13, 1988, abandoned, which is a continuation of Ser. No. 939,926, Dec. 9, 1986, abandoned.

[51] Int. Cl.$^5$ .............................................. G01N 1/22
[52] U.S. Cl. ........................................ 422/84; 73/23.3; 128/719; 436/132; 436/900; 422/85
[58] Field of Search ................... 422/84, 85; 436/132, 436/900; 128/719; 73/23, 27 R, 23.3

[56] References Cited

U.S. PATENT DOCUMENTS

| | | | |
|---|---|---|---|
| 3,877,291 | 4/1975 | Hoppesch et al. | 422/84 X |
| 3,940,251 | 2/1976 | Jones et al. | 422/84 |
| 4,617,821 | 10/1986 | Yokoyama et al. | 422/84 X |
| 4,626,686 | 12/1986 | Pompei et al. | 374/124 X |

Primary Examiner—Robert J. Warden
Assistant Examiner—Timothy M. McMahon
Attorney, Agent, or Firm—Irene J. Frangos

[57] ABSTRACT

An air-borne chemical sensor system includes a motor and impeller to draw an air sample into a housing containing a sensor which will provide a signal for display related to the amount of a particular air-borne chemical in a given air sample. The system is controllable by different duration activation of a single activating switch which can further control a secondary function, such as a flashlight.

4 Claims, 2 Drawing Sheets

AIR-BORNE ALCOHOL SENSOR

This is a continuation, of application Ser. No. 07/463,930, filed Jan. 8, 1990, entitled Air-Borne Alcohol Sensor now abandoned, which is a continuation, of application Ser. No. 07/244,580, filed Sept. 13, 1988, now abandoned, entitled AIR-BORNE ALCOHOL SENSOR, which is a continuation of Ser. No. 06/939,926, filed Dec. 9, 1986, entitled AIR-BORNE ALCOHOL SENSOR, now abandoned.

BACKGROUND OF THE INVENTION

In most major industrialized countries, alcohol abuse has become a major problem. On the road, in business, and at large social functions, such as sporting events. To help reduce this problem, many countries have established levels of blood alcohol above which an individual is considered legally intoxicated.

While the exact level of alcohol in the blood is only possible from an actual blood sample, it has been determined that a sufficient correlation exists between the blood alcohol level and the exhaled alcohol in an individual's breath to allow a measurement of the latter to be legal evidence of the former. The breath alcohol concentration is often expressed as an equivalent percentage of the blood alcohol concentration and is denoted by percent BAC. To measure percent BAC, a number of systems have been developed such as those utilizing a wheatstone bridge with catalytic resistance leg as shown in U.S. Pat. No. 3,764,270 granted to Collier, et al on Oct. 9, 1973, and those using a fuel cell sensor as shown in U.S. Pat. No. 3,940,251 granted to Jones, et al on Feb. 24, 1976.

While these systems are able to accurately determine percent BAC, they all require the cooperation of the individual and/or are such complex devices to operate that the individual being tested will attempt to thwart the device. For example, the patented devices supra. require the driver to exhale a deep breath into a tube which transfers the breath sample to the alcohol measuring sensor. There is no way of being able to test a driver's breath without cooperation, participation, or knowledge with these systems.

Ideally, a tester should be able to rapidly screen individuals with a device which is easily operated and unobtrusive. For example, police officers should be able to screen stopped drivers or drivers at roadblocks even where breath mints or other breath odor reducers are being used. Further, unconscious individuals should easily be tested after a traffic accident or in an emergency room environment. Similarly, it would be desirable to screen employees in hazardous occupations as they report to work or to prevent access by intoxicated individuals to bars. The system should allow for easy, single-handed operation which is totally automatic. In most situations, the accuracy of such an ideal device need not be high since it would be used primarily for screening to be followed by a more accurate measurement for legal purposes after the initial screening.

Further, it would be ideal if the testing device appeared to have some other function than the alcohol testing one. This would help allay suspicions and would help prevent antagonizing those who are intoxicated.

SUMMARY

The present invention provides an air-borne chemical sensor, specifically for the chemical alcohol, which can be operated with one hand to initiate automatic sampling, testing, and display of the chemical concentration.

The present invention further provides a dual function device, specifically an air-borne alcohol sensor and flashlight, which can be operated with one hand, and more specifically by one switch.

The present invention still further provides a visual display which can be digital or logarithmic to indicate the chemical concentration, and which can be color coded to indicate zero, medium, or high levels of concentration.

The present invention even further provides an air-borne chemical sensor system which includes a power supply monitored by a low power, intermittent indicator system.

The invention, together with further advantages and features thereof, may best be understood by reference to the following description taken in conjunction with the accompanying drawings.

DESCRIPTION OF THE PREFERRED EMBODIMENT

During the course of the description of the present invention, reference will be made primarily to block diagrams of the apparatus. The various block units which are utilized are primarily standard electronic units or consist of conventional electronics, and sufficient description of them will be given to enable one skilled in the art to understand the nature and functioning of the apparatus. In several instances, in order to aid in an appreciation of the operation of the present invention, specific schematic circuits are disclosed for certain of the block units. It is to be understood that these specific schematic circuits have been simplified as would be evident to those skilled in the art, and further are intended solely as illustrative of the type of circuits usable in the present invention and many changes and modifications will be readily apparent.

Figure 1:
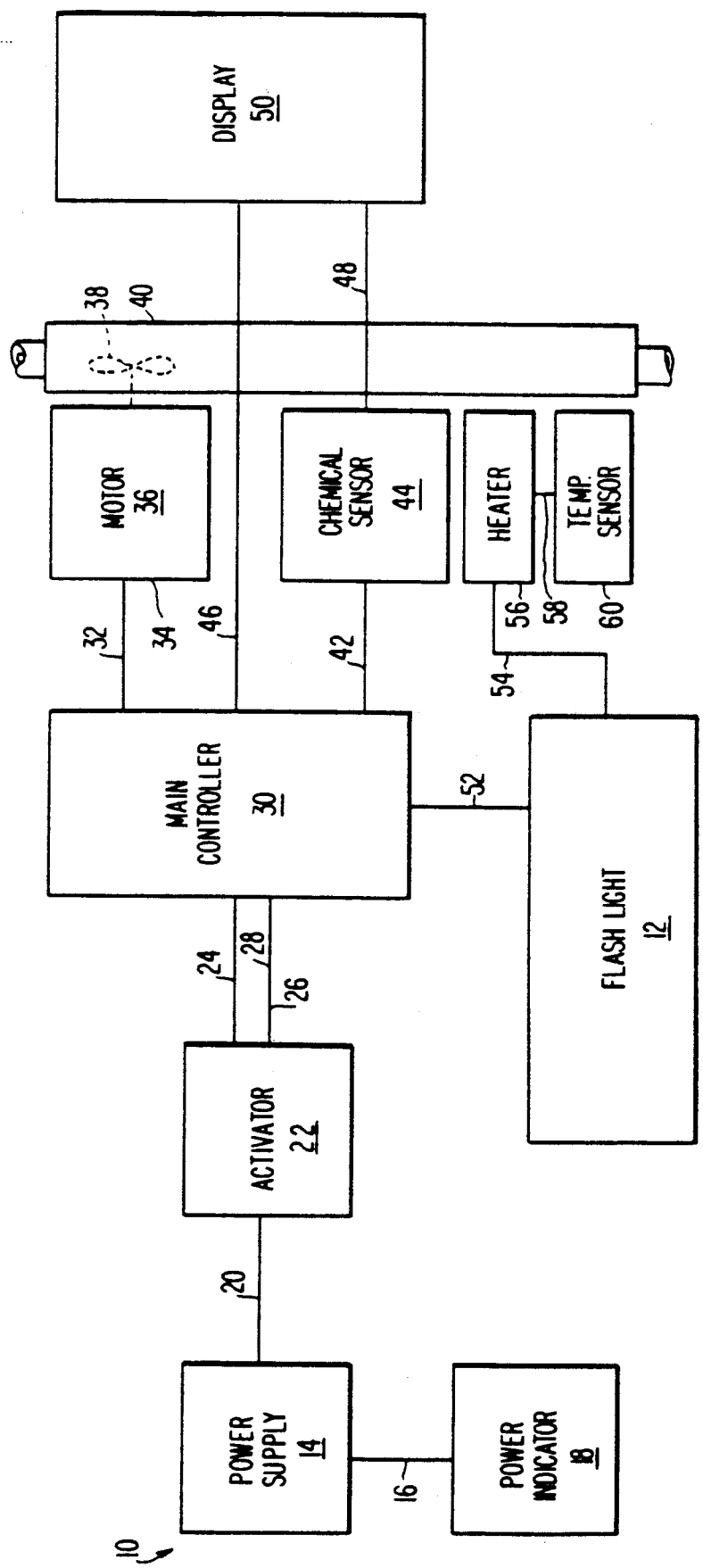
FIG. 1 is a block diagram of the present invention.

Referring now to FIG. 1, therein is shown the alcohol sensor system 10 and the flashlight 12. It should be noted, while it is not shown, that the alcohol sensor system is coaxial with the flashlight 12 in a housing which resembles a police standard flaslight.

The alcohol sensor system 10 includes a power supply 14 connected by a lead 16 to a power indicator 18. The power supply 14 is further connected by a lead 20 to an activator 22, which contains a switch and a conventional RC time delay circuit. The activator 22 is connected by lead 24, lead 26, and clock lead 28 to the main controller 30.

The main controller 30 is connected by leads 32 and 34 to a motor 36 which drives an impeller 38 which is disposed in a housing 40.

The main controller 30 is further connected by a lead 42 to a chemical sensor 44 which is an alcohol sensitive fuel cell disposed in the housing 40. The impeller 38 circulates the air-borne alcohol past the chemical sensor 44. Both the main controller 30 and the chemical sensor 44 are connected by leads 46 and 48, respectively, to a display 50.

In the preferred embodiment, the display 50 is a multi-color bar graph display of the type exemplified by the HDSP-4832 device manufactured by Hewlett Packard. The display 50 provides ten LED bar lamps, three of which are green, four are yellow and three are red.

When used in testing an individual, a display 50 reading of green would indicate that there is little likelihood of intoxication with an approximate BAC of between 0 and 0.05 BAC. Yellow would indicate further testing may be desired with an approximate BAC of 0.08 to 0.16. Red would indicate a high likelihood of intoxication with a BAC ranging from 0.16 or above. In taking the samples, it should be noted that the sensor should be located about six inches away from the individuals mouth.

The main controller 30 is still further connected to the flashlight 12 by lead 52. The flashlight 12 is connected by a lead 54 to a heater 56. The heater 56 is further connected by a lead 58 to a temperature sensor 60.

The chemical sensor 44, the heater 56 and the temperature sensor 60 abut each other and the heater 56 abuts the chemical sensor 44.

Figure 2:
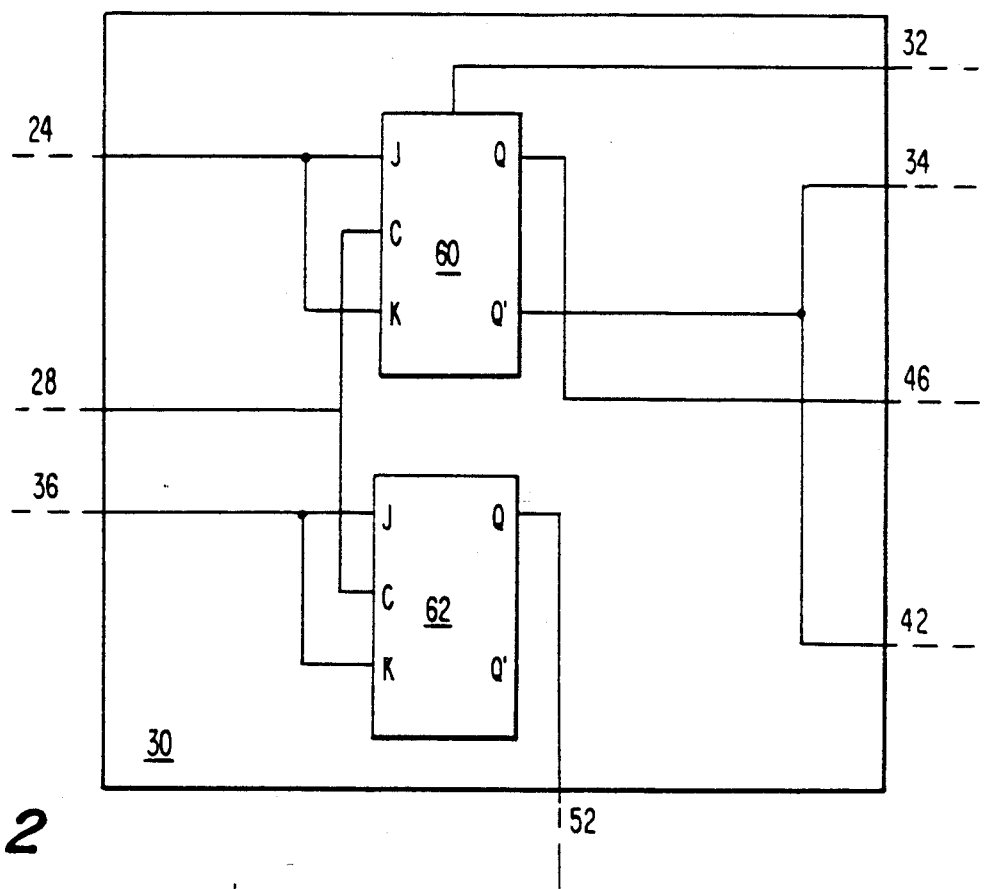
FIG. 2 is a simplified schematic of the control portion of the present invention.

Referring now to FIG. 2, therein is shown the main controller 30 which consists of two JK flipflops 60 and 62. The flipflop 60 has its JK inputs connected to lead 24 and its clock input connected to lead 28. A lead 32 from the motor 36 is further connected to the set input of the flipflop 60. The Q output is connected to the lead 46 and the Q' output is connected to the leads 34 and 42.

The flipflop 62 has its J and K inputs connected to the leads 26, its clock input connected to the lead 28 and its Q output connected to the lead 52.

Figure 3:
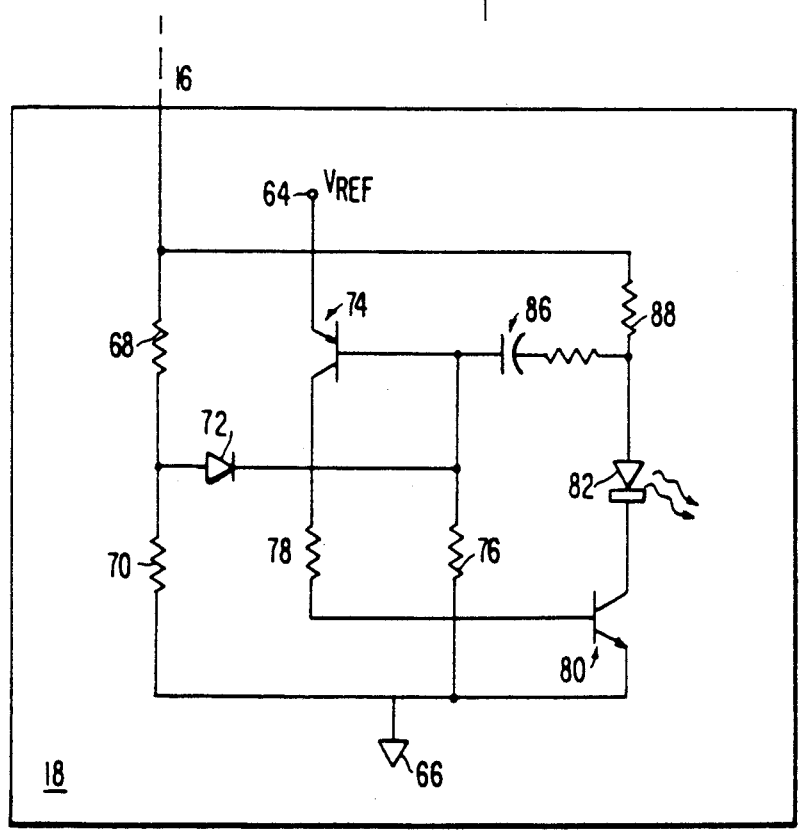
FIG. 3 is a simplified schematic of the power supply indicator of the present invention.

Referring now to FIG. 3, therein is shown a power indicator 18 which contains a fixed voltage reference 64 and a ground 66 which are connected to other parts of the alcohol sensor system 10 as would be evident to those skilled in the art. The lead 16 is connected to the ground 66 by a voltage divider made up of precision resistors 68 and 70. Resistors 68 and 70 are connected by a diode 72 to the base of a PNP transistor 74 and a resistor 76 which in turn is connected to the ground 66.

The emitter of the transistor 74 is connected to the voltage reference 64 and its collector is connected via a resistor 78 to the base of an NPN transistor 80 which makes up the other transistor of an astable multivibrator. The emitter of the transistor 80 is connected to the ground 66 and the collector is connected to a light emitting diode 82 and thence by a resistor 84 and a capacitor 86 to the base of the transistor 74. The light emitting diode 82 is further connected by a resistor 88 to the power supply by the lead 16.

As would be evident to those skilled in the art, the power supply 14 would be connected by leads to power all of the necessary electronic components, but these leads are not shown so as to simplify the drawings.

The operation of the entire system shown in FIG. 1 may be divided into three parts although the latter two may overlap; quiescent, sensing and secondary function. In the quiescent state, the power supply 14, which is generally a series of batteries, supplies power at a very low level to the power indicator 18, logic highs over the leads 24 and 28 to the main controller 30, and a logic low over the lead 26 to the main controller 30. In turn, the main controller 30 provides highs over leads 34 and 42 to the motor 36 and the chemical sensor 44, respectively, so the motor 36 is off and the chemical sensor 44 is held in a short-circuited condition. Lows are provided over leads 46 and 52 so the display 50 and flashlight 52, respectively, are in their off conditions. With the flashlight 12 off, the heater 56 and the temperature sensor 60 are also inoperative.

In FIG. 3, it may be seen that in the quiescent state, the JK inputs of flipflop 60 are high and the JK inputs of the flipflop 62 are low to cause the Q outputs to be low and the Q' outputs to be high.

In FIG. 3, it may be seen that as long as the voltage at the connection of resistors 68 and 70 remain above a predetermined level established by the value of the resistors, the transistors 74 and 80 will be quiescent and the light emitting diode 82 will not emit any light.

To start chemical sensing, a switch in the activator 22 is activated momentarily. This causes the inputs to the flipflop 60 to go low and the inputs to the flipflop 62 to go high while starting the time delay of the RC circuit in the activator 22 to provide a typically 0.5 second signal delay to the clock inputs of the flipflops 60 and 62.

In the chemical sensor 44, the low from the Q' output of the flipflop 60 causes the short circuit across the fuel cell to terminate and the fuel cell to start providing an output proportional to the alcohol in the air passing by the fuel cell. The low further turns on the motor 36 to cause the impeller 38 to pass air through the housing 40. The motor 36 has an RC circuit which further provides that it will remain on for at least five seconds to provide a predetermined volume sample of air to the chemical sensor 44. While the motor 36 is operational, a high is provided to the set input of the flipflop 60 via lead 32 to prevent the sensing cycle from terminating.

The display 50 is turned on by the high out of the Q output of flipflop 60 and provides a visual indication thereof. This is generally a green light at the lowest bar level of the color bar graph display.

Since the activation is only momentary, the state of the lead 28 does not change and thus the Q output of the flipflop 62 remains low and the flashlight 12 remains off along with the heater 56 and the temperature sensor 60.

As would be evident to those skilled in the art, a momentary activation of the activator 22 after the five second motor 36 activation period will cause the flipflop 60 to change state. The change of state of the flipflop 60 would then cause the short circuit across the chemical sensor 44, and the motor 36 and the display 50 to turn off.

To operate the secondary function, the flashlight 12, the switch in the activator 22 is activated for longer than the RC circuit imposed time delay which causes the flipflops 60 and 62 to be clocked. At this point, the flipflop 60 will not change state since its inputs would be low. The flipflop 62 would change state so as to put a high on the lead 52 and cause the flashlight 12 to light.

When the flashlight 12 is lit, the heater 56 and the temperature sensor 60 will be powered up. The chemical sensor 44 is a fuel cell which will recover most rapidly at a temperature of 40° C. Thus, if a number of readings in succession are desired, the flashlight 12 is activated to cause the heater 56 to heat the chemical sensor 44. If the temperature exceeds 40° C., the temperature sensor 60 shuts off the heater 56.

Again, as would be evident to those skilled in the art, by activating the switch in the activator 22 for longer than the 0.5 second time delay, the flipflop 62 may be made to change state and to turn the flashlight 12, the heater 56, and the temperature sensor 60 off.

As long as the power supply 14 is above a predetermined level for proper operation of the alcohol sensor system 10, the power indicator 18 is substantially inoperative. When the voltage at the junction of resistors 68 and 70 decrease to a certain predetermined level indicating that the power supply, generally some batteries, is running low, the transistors 74 and 80 alternately turn on and off at a rate determined by the capacitor 86 and resistor 84 to hunt for the non-existent stable state which defines an astable multivibrator. This oscillation causes an intermittent flashing of the LCD 82 to indicate that the power level, or the batteries, is low.

The advantage of the power indicator 18 as configured is that it has a low power draw at all times and with the intermittent flashing of the LCD 82, a low battery indication can be provided for three one and one-half volt batteries for approximately one week before the LED no longer flashes.

While the preferred embodiment of the present invention has been shown and described, it would be obvious to those skilled in the art that changes and modifications may be made without departing from the spirit and scope of the invention. For example, the display 50 may be either a direct or logarithmic readout with the latter being utilized where wider dynamic range is desired. Therefore, it is to be understood that all matter set forth herein or shown are to be interpreted in an illustrative and not a limiting sense.

I claim:

1. A combined airborne alcohol sensor and independently activatable flashlight system comprising:
   a housing containing a flashlight, and air impeller for passing sample air through the housing, a motor coupled to the impeller and connected to a first RC circuit, an alcohol specific electrochemical fuel cell for analyzing the alcohol content of the sample air, a control means, and a power supply for supplying electrical power to the system, disposed in the housing;
   a visual display means connected to the fuel cell wherein the display means provides an indication proportional to the concentration of alcohol as determined by the fuel cell;
   an activator comprising a switch and a second RC time delay circuit connected to the power supply and the control means;
   the control means being connected to the flashlight, motor, fuel cell and display means and comprising at least two flip flops, the flip flops being connected to a clock input which in turn is connected to the second RC time delay circuit so that the system may be in a quiescent state, alcohol sensing function or secondary flashlight function depending on the period of actuation of the activator switch;
   wherein a momentary actuation of the activator switch while the system is in the quiescent state or secondary function causes the system to start the chemical sensing function by turning on the motor which will operate for a predetermined period of time as provided by the first RC circuit and causing the impeller to pass sample air by the fuel cell; whereby the fuel cell provides an output on the display means proportional to the alcohol in the air passing by the fuel cell;
   wherein a momentary actuation, after the predetermined period of time provided by the first RC circuit, of the activator while the system is in the sensing function turns the sensing function off;
   wherein an actuation of the activator switch for a period longer than a period of time imposed by the second RC time delay circuit while the system is in the quiescent state or sensing function starts the secondary flashlight function; and
   wherein an actuation of the activator switch for a period longer than a period of time imposed by the second RC time delay circuit turns off the secondary function.

2. The combined airborne alcohol sensor and independently activatable flashlight system of claim 1 which also comprises a heater connected to the control means, and to a temperature sensor and disposed proximately to the fuel cell in the housing, wherein the heater is caused to operate by an actuation of the activator switch for a period longer than the period of time imposed by the second RC time delay circuit in conjunction with the secondary flashlight function.

3. The combined airborne alcohol sensor and independently activatable flashlight system of claim 1 which also comprises a power indicator connected to the power supply which is capable of indicating when the power level is low.

4. The combined airborne alcohol sensor and independently activatable flashlight system of claim 1 wherein the visual display means includes a bar graph indicator which provides a light emitting, multi-color indication.

* * * * *